United States Patent [19]

Murphy

[11] Patent Number: 5,428,474
[45] Date of Patent: Jun. 27, 1995

[54] VISION PROTECTION DEVICE INCORPORATING CARRIER LENSES

[75] Inventor: Peter J. Murphy, Flower Hill, N.Y.

[73] Assignee: Designs For Vision, Inc., Ronkonkoma, N.Y.

[21] Appl. No.: 109,616

[22] Filed: Aug. 20, 1993

[51] Int. Cl.$^6$ .......................... G02C 7/10; G02C 7/08; G02C 7/16

[52] U.S. Cl. ..................... 359/361; 351/163; 351/165; 359/409

[58] Field of Search ............... 359/350, 361, 409, 891, 359/892; 351/158, 163, 165

[56] References Cited

U.S. PATENT DOCUMENTS

| | | | |
|---|---|---|---|
| 1,771,451 | 7/1930 | Suzuki et al. | 351/165 |
| 1,802,424 | 4/1931 | Hitchiner | 351/165 |
| 2,037,327 | 4/1936 | Hubbell | 351/165 |
| 2,043,840 | 6/1936 | Singer | 351/165 |
| 2,139,213 | 12/1938 | Verre | 351/165 |
| 4,311,368 | 1/1982 | Saito et al. | 351/165 |
| 4,952,046 | 8/1990 | Stephens et al. | 351/163 |
| 5,076,682 | 12/1991 | Pasfield | 351/158 |
| 5,129,717 | 7/1992 | Feinbloom | 351/158 |
| 5,235,358 | 8/1993 | Mutzhas et al. | 351/163 |
| 5,291,229 | 3/1994 | Feinbloom | 351/158 |

*Primary Examiner*—Martin Lerner
*Attorney, Agent, or Firm*—Plevy & Associates

[57] ABSTRACT

An apparatus for protecting the eyes of a dental or medical practitioner from exposure to ultraviolet radiation during the illumination of a surgical site or other area of interest includes first and second carrier lenses positioned within a suitable frame. The first carrier lens comprises first and second regions wherein the first region is adapted to transmit substantially all visible light incident thereon and wherein the second region is adapted to absorb or reflect all ultraviolet light incident thereon and at least some light incident thereon having a wavelength above 400 nm. At least a portion of the second carrier lens is also adapted to absorb or reflect both ultraviolet light and at a portion of light incident thereon having a wavelength above 400 nm. This configuration protects the practitioner from exposure from the ultraviolet portion of the electromagnetic spectrum but permits the practitioner to view an area of interest via a non-absorbing region of at least one lens when a clear view of the area is desired. Each carrier lens is also adapted to receive a magnifying lens to provide the practitioner with a magnified image of an area under inspection without necessitating removal of the protective device.

16 Claims, 2 Drawing Sheets

VISION PROTECTION DEVICE INCORPORATING CARRIER LENSES

BACKGROUND OF THE INVENTION

This invention relates generally to vision protection devices, and more particularly, to a lens system for dentists, surgeons, and other practitioners which system is adapted to provide protection from ultraviolet radiation during surgical and diagnostic procedures.

The retina of the human eye is a thin structure of extreme complexity. The receptors, which may number 125,000,000 in each eye, comprise a large number (about 95%) of rods and a small number (about 5%) of cones. In a rod-free depression of the retina known as the fovea centralis, a small central bouquet of about 2,000 cones are packed together into a hexagonal array having a density of about 150,000 per square millimeter. The cones in this area are capable of dissecting the finest details of the optimal retinal image. The rods and cones are synaptically connected to the bipolar cells, which in turn relate to the ganglion cells, whose axons constitute the optic nerve fibers. There is a high degree of convergence, however, in that the 125,000,000 receptors ultimately feed into only 1,000,000 nerve fibers of the flexible optic nerve, which therefore constitutes the principal bottleneck of information flow in the visual system. The convergence ratio for the fovea is about 1:1, helping to preserve the high detail vision of this region, while in the peripheral region of the retina, the ratio is many thousands to one, leading to high sensitivity at the expense of resolving power.

When the sensory layer of the retina separates from the pigment layer, retinal detachment is said to occur. This may result as a complication of some disease, or may be caused by repeated exposure to ultra violet radiation (light having a wavelength of between 10-380 nm). The detachment is partial at first, but without medical attention, almost always becomes complete, resulting in total and permanent blindness in the affected eye. At first, the patient may "see" flashes of light. Then, the patient may experience the sensation of a curtain gradually moving across the eye. The field of vision becomes progressively cloudy, until vision is lost. The progressive nature of retinal detachment is due to the gradual seepage of fluid from the large vitreous cavity into the space between the two layers of the retina. As more fluid seeps through the original hole in the retina, more of the sensory layer of the retina is separated from the pigment layer, until the detachment is complete.

As indicated above, repeated exposure to ultra-violet radiation can lead to retinal detachment and, if untreated, eventually to blindness. Accordingly, it is important to protect the eyes whenever and wherever exposure to sources of UV radiation is anticipated. Tanning booths, for example, typically provide their patrons with special eye pieces which fit over the eyes and filter out the ultra-violet radiation emitted therein. Because of the intensity of light used in such booths, the eyes of the patron would otherwise be exposed to UV radiation even when closed.

Light sources which emit radiation in the UV range are also utilized in many dental and medical procedures. For example, UV light is typically employed to cure the epoxies or cements used in dental reconstruction or implantation procedures. During surgical or operating room procedures, in which localized, high intensity light is required, a "cold light" source is often employed. Essentially, the cold light source comprises a fiber optic cable which is illuminated by a high intensity high wattage lamp. The light source of the lamp is positioned to illuminate an inlet port of a fiber optic cable, which cable may be a few feet or more in length. The surgeon or dentist uses the fiber optic cable as a light source and he can therefore direct the light emanating from the outlet end of the fiber optic cable to any desired position. Because the amount of light needed for dental as well as surgical procedures is substantial, lamp sources such as halogen, or xenon or other high intensity lamps are employed. Each of these sources emit a sizable power in continuous ultraviolet radiation.

From the foregoing discussion, it can be seen that it in many situations dental or medical practitioners are exposed to significant levels of UV radiation. For this reason, the practitioner must wear glasses or some other visual aid to filter out the harmful radiation. One disadvantage of such visual aids, however, is that they may diminish the clarity or otherwise obscure the practitioner's view of area of the patient under inspection. Accordingly, such aids are often removed when the practitioner desires a clearer view. A further disadvantage of such visual aids is that they do not accommodate the use of magnifying attachments which aid the practitioner in focusing on those areas of particular interest during a given surgical or diagnostic procedure.

Accordingly, it is an object of the present invention to provide a visual aid device for use by dental or medical practitioners which device adequately protects the eyes of the practitioner from the harmful effects of ultraviolet radiation but which also permits the practitioner to obtain an unfiltered view when desired.

It is a further object of the present invention to provide a visual aid which is adapted to incorporate attachments having magnifying or other optical properties so that the device may be employed during typical surgical or diagnostic procedures.

SUMMARY OF THE INVENTION

A visual aid apparatus for protecting the eyes of a dental or medical practitioner from harmful ultraviolet radiation during certain surgical and diagnostic procedures comprises first and second lenses positioned within a suitable frame. The first lens comprises first and second regions wherein the first region is adapted to transmit substantially all visible light incident thereon and wherein the second region is adapted to absorb or reflect all ultraviolet light incident thereon. The second region is also adapted to absorb or reflect at least some light incident thereon having a wavelength above 400 nm. At least a portion of the second carrier lens is also adapted to absorb or reflect all ultraviolet light and a portion of the light incident thereon having a wavelength above 400 nm or below. This configuration protects the practitioner from exposure from the ultraviolet portion of the electromagnetic spectrum but permits an area of interest to be viewed via a non-absorbing region of at least one lens when a clear view of the area is desired. Each carrier lens is also adapted to receive a magnifying lens to provide the practitioner with a magnified image of an area under inspection without necessitating removal of the protective device.

DETAILED DESCRIPTION OF THE INVENTION

Figure 1:
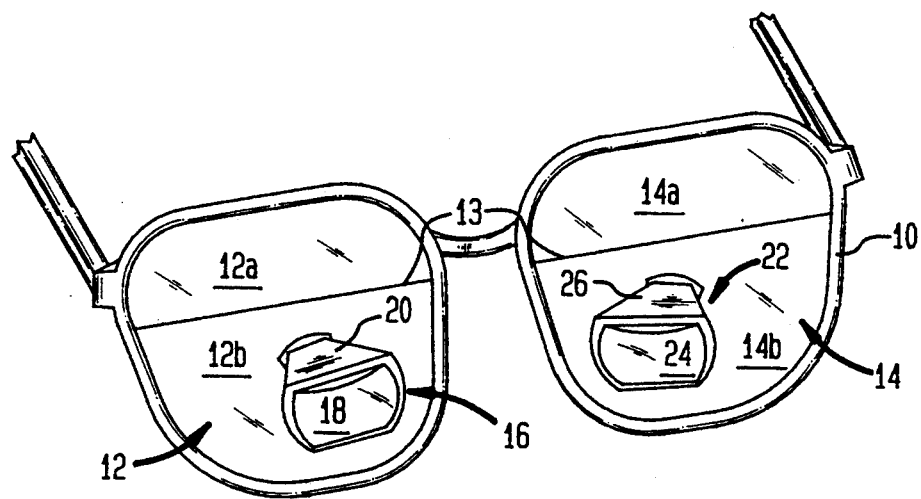
FIG. 1 is a perspective view of a visual aid apparatus constructed in accordance with an illustrative embodiment of the present invention.

Referring to FIG. 1, there is shown a spectacle frame 10. The spectacle frame 10 has two lenses 12 and 14 indicative of a lens for the right eye and one for the left eye, respectively. Each lens 12 and 14 may be a prescription type lens which accommodates the far distance or near distance prescription of the practitioner who wears the spectacle frame. As seen in FIG. 1, lens 12 is divided into upper region 12a and lower region 12b. Similarly, lens 14 is also divided into upper and lower section 14a and 14b. In accordance with the aforementioned objective of the present invention, which is to protect the eyes of the practitioner from ultraviolet radiation encountered during certain surgical and diagnostic procedures, regions 12b and 14b are constructed so that it will not transmit light below a predetermined wavelength.

Essentially, materials adapted to selectively transmit light at certain wavelengths but to absorb or reflect others are known as absorption filters in the photographic art and are commercially available. Such filters may, for example, be manufactured by adding metallic salts to clear glass. Where, as here, the object is to prevent the transmission of ultraviolet radiation, it will be readily apparent that at a minimum, the material should be adapted to reflect or absorb light having a wavelength 380 nm or below. However, given such considerations as commercial availability and other economic factors, it will be readily appreciated that materials or coatings which absorb light at higher wavelengths, including wavelengths which are in the visible range may be utilized as well. Red, orange, and yellow glasses, for example, all transmit the red and near infrared and have a fairly sharp cutoff. The position of this cutoff determines the apparent color of the filter.

In the illustrative embodiment depicted in FIG. 1, an orange glass filter which absorbs or reflects all light below 530 nm is utilized for regions 12b and 14b. It will be appreciated that the threshold between absorption and transmittance will vary with the properties and thickness of the material utilized. So long as the material transmits at least some light in the visible range and absorbs all light in the ultraviolet range, however, it may be employed. It should be noted that heretofore, the practitioner relying upon protective glasses manufactured from materials such as colored glass or plastic was required to remove the same to obtain a clear, non-filtered view of an area under investigation. To obviate this, the present invention incorporates at least one clear region in at least one lens which is adapted to transmit all wavelengths of visible light (roughly, between 400 and 700 nm). In the embodiment illustrated in FIG. 1, both upper region 12a and 14a are substantially clear and are adapted to transmit therethrough all visible light incident thereon.

In permitting the dental or medical practitioner to look through either section as desired, the device of the present invention need not be removed when the ultraviolet source is removed or energized, as the case may be. Moreover, when configured with lenses of the prescriptive type, the device of the present invention makes it unnecessary for the practitioner to switch from a pair of non-protective prescription glasses to a pair of filtering glasses when a clearer view is desired.

With continuing reference to FIG. 1, it will be observed that lenses 12 and 14 may be optionally configured as carrier lenses such that respective telescope assemblies 16 and 22 may be positioned within apertures drilled therethrough. Visual aids utilizing apertured carrier lenses to position lens assemblies in alignment with each eye are known. See for example, U.S. Pat. No. 5,129,717 entitled ADJUSTABLE TELESCOPIC ALIGNMENT APPARATUS FOR USE WITH A CARRIER LENS, issued to Richard E. Feinbloom on Jul. 14, 1992 and assigned to the assignee herein.

As can be seen in FIG. 1, each telescope assembly includes a magnifying lens 18 or 24, the power of which lens may be on the order of 2X, selected to provide the practitioner with a desired degree of magnification during the examination of a patient or during the performance of a surgical procedure. It will of course be understood that any means for securing lenses 18 and 24 to the carrier lenses may be employed. In the illustrated embodiment, magnifying lenses 18 and 24 are received within the bores of corresponding sleeve members 20 and 26. The sleeve members may be cemented or otherwise securely fastened in place at the laboratory within the apertures (not shown) of the carrier lenses. Although a fixed mounted telescope construction is depicted in the illustrative embodiment of FIG. 1, it should be understood that any suitable telescopic lens construction, such as the movable arrangement depicted in the aforementioned U.S. Pat. No. 5,129,717, may be employed in accordance with a carrier lens embodiment of the present invention. Moreover, the telescope need not be of a fixed power but could also be configured in adjustable form to provide different degrees of magnification as desired.

Figure 2:
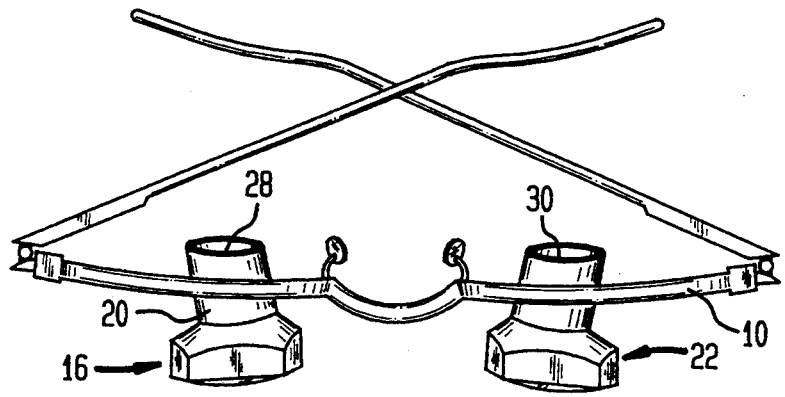
FIG. 2 is a plan view of the visual aid apparatus depicted in FIG. 1.
Figure 3:
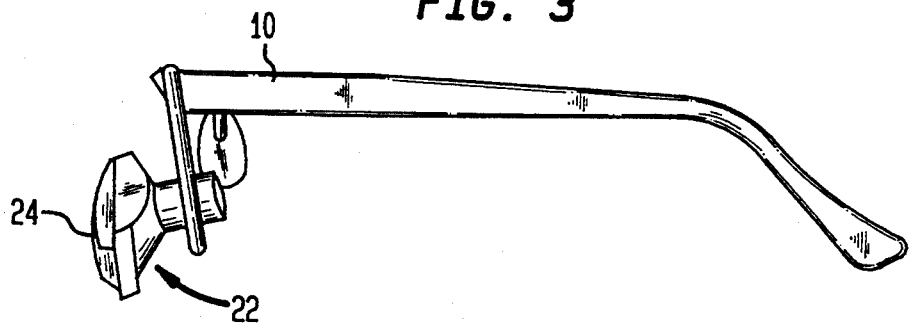
FIG. 3 is a side elevation view of the visual aid apparatus depicted in FIG. 1.

As seen in FIGS. 2 and 3, the telescope assemblies may be oriented in a converging manner and directed downwardly to provide a binocular image of the area of the patient under investigation. The chosen location and orientation of the telescope assemblies, however, may be modified in accordance with the preference of the wearer. For example, in a bioptic configuration, the assemblies are mounted high in the carrier lens so that the telescope is out of the way unless needed.

With particular reference to FIG. 2, it can be seen that each telescope assembly may also be provided with a prescription type lens 28 or 30 to accommodate the far distance or near distance prescription of the practitioner. For this purpose, the bore at the proximal end of the sleeve member is stepped to a reduced diameter to provide an abutment surface (not shown) for bonding such lenses thereto. It will, of course, be readily appreciated by those skilled in the an that lenses 28 and 30 may also be constructed of or coated with materials which are adapted to absorb ultraviolet radiation.

Figure 4:
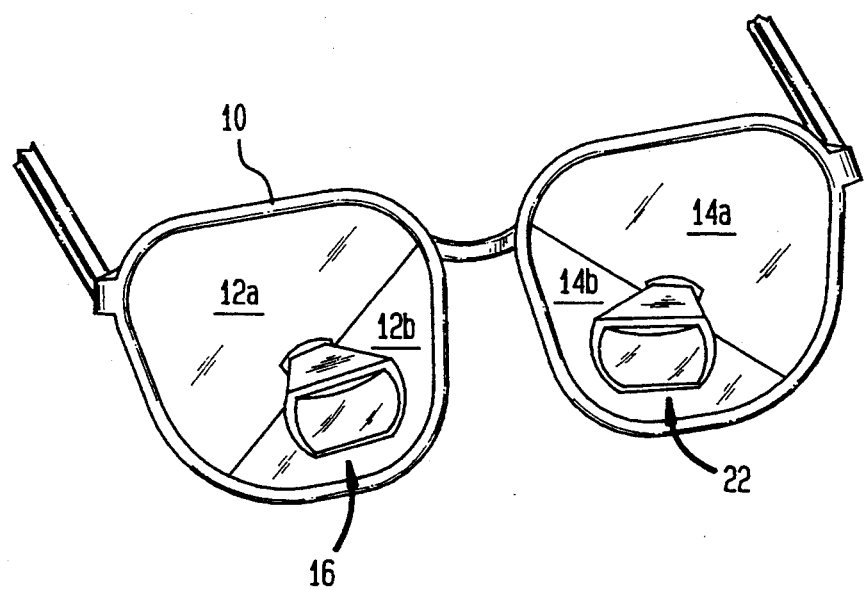
FIG. 4 is a perspective view of a visual aid constructed in accordance with an alternate embodiment of the present invention.

Turning again to FIG. 1, it will be observed that regions 12a and 12b are configured as two independent sections with a seam 13 extending therebetween. It should be understood, however, that the lens 12 may also be integrally formed from a single piece of glass or plastic wherein the filtered region is provided by coating a portion thereof. It should also be noted that the dimensions, shape, and relative positions of regions 12a and 12b may be easily modified to provide the practitioner with any desired combination of filtered and unfiltered fields of view. For example, regions 12a and 12b might be reversed so that 12a is filtered and 12b unfiltered. As a further example, the line of demarcation between the filtered and unfiltered fields of view might appear diagonally, as shown in FIG. 4.

Figure 5:
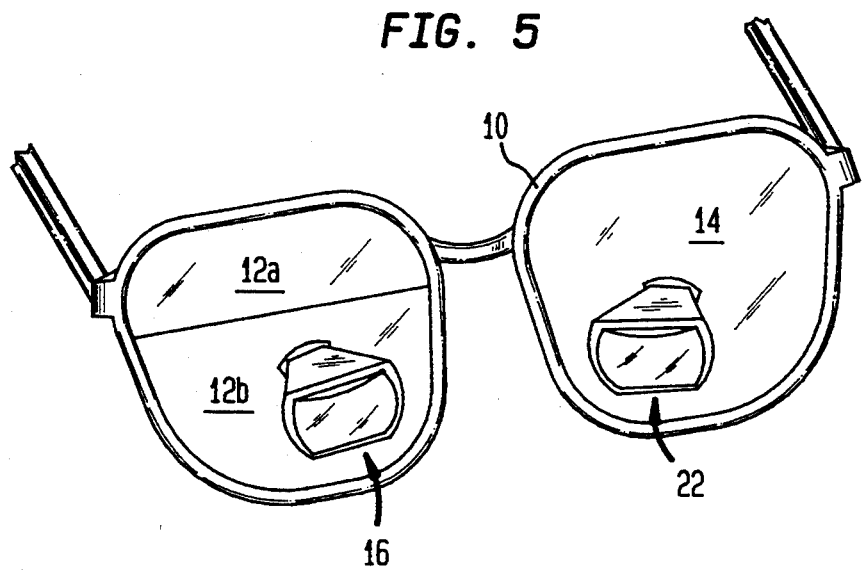
FIG. 5 is a perspective view of a visual aid constructed in accordance with yet another embodiment of the present invention.

Although lenses 12 and 14 appear identical in terms of the location and relative positions of the filtered and unfiltered regions, it will be readily apparent that the present invention is not limited to this configuration. Thus, in accordance with a further embodiment of the present invention, only one of the lenses need include an unfiltered region. Thus, in FIG. 5, where like numerals represent like elements, only region 12a is unfiltered, while region 12b and lens 14 in its entirety are designed to absorb or reflect ultraviolet radiation.

Although the present invention has been described with reference to particular embodiments, workers skilled in the art will recognize that changes may be made in form and detail without departing from the spirit and scope of the invention.

What is claimed is:

1. Apparatus for protecting the eyes of a person from exposure to ultraviolet radiation, comprising:
   a first lens having a first region and a second region, wherein said first region is transparent to substantially all visible light and said second region filters light having a wavelength below 530 nm and is substantially transparent to visible light having a wavelength exceeding 530 nm;
   a second lens, wherein at least a portion of said second lens filters light having a wavelength below 530 nm and is substantially transparent to visible light having a wavelength exceeding 530 nm;
   means for positioning said first lens and said second lens at a selected distance relative to the eyes of said person; and
   first and second magnifying means for providing a person viewing therethrough with a magnified image, wherein said first lens and said second lens are each a carrier lens, each carrier lens defining an aperture therein for receiving a corresponding one of said magnifying means.

2. Apparatus according to claim 1, wherein said second lens is adapted to absorb or reflect at least some light incident thereon having a wavelength exceeding 400 nm.

3. Apparatus according to claim 2, wherein said second lens are adapted to absorb or reflect light having a wavelength below 530 nm.

4. Apparatus according to claim 1, wherein said second lens includes a first region substantially transparent to all visible light.

5. Apparatus according to claim 4, wherein said first lens and said second lens both have a top edge and an opposite bottom edge, said second region of said first lens and said portion of said second lens being disposed proximate said bottom edge of said first lens and said second lens, respectively.

6. Apparatus according to claim 1, wherein said first region and said second region integrally comprise said first lens.

7. Apparatus according to claim 1, wherein said first lens and said second lens are corrective lenses.

8. Apparatus according to claim 1, wherein each of said magnifying means includes a sleeve member defining an axial bore therethrough and a magnifying lens disposed within a distal portion of said axial bore.

9. Apparatus according to claim 9, wherein each of said magnifying means further includes a corrective lens aligned with said axial bore adjacent a proximal portion thereof.

10. Apparatus according to claim 10, wherein said corrective lenses filter substantially all ultraviolet light.

11. Apparatus according to claim 1, wherein said positioning means comprises a frame adapted to be worn by said person and defining respective apertures for accommodating said first lens and said second lens.

12. Apparatus for protecting the eyes of a person from exposure to ultraviolet radiation during the illumination of an area of interest, comprising:
   a first carrier lens having a first region and a second region, said first region being transparent to substantially all visible light and said second region being adapted to filter substantially all ultraviolet light below a predetermined frequency;
   a second carrier lens, at least a portion of said lens being adapted to filter substantially all ultraviolet light below said predetermined frequency;
   frame means for positioning said first carrier lens and said second carrier lens at a selected distance relative to a person's eyes and in alignment therewith, whereby the person may selectively view the area of interest via said second region; and
   first and second magnifying means each associated with a corresponding one of said first carrier lens and said second carrier lens, wherein each of said magnifying means includes filtering means for filtering substantially all ultraviolet light.

13. Apparatus according to claim 12, wherein each of said magnifying means comprises a sleeve member defining an axial bore therethrough and a magnifying lens disposed within a distal portion of said axial bore.

14. Apparatus according to claim 13, wherein said filtering means comprises a corrective lens adapted to filter substantially all of said ultraviolet light, said corrective lens being aligned with said axial bore adjacent a proximal portion thereof.

15. Apparatus according to claim 14, wherein said second region of said first lens and said portion of said second lens are adapted to absorb or reflect light at least some light incident thereon having a wavelength above 400 nm.

16. Apparatus for protecting at least one eye of a person from exposure to ultraviolet radiation comprising:
   eyeglass frames;
   a first carrier lens and a second carrier lens supported by said eyeglass frames, wherein said first carrier lens and said second carrier lens each have a region adapted to filter ultraviolet light; and
   an optical telescope assembly having filtering means for substantially filtering all ultraviolet light, coupled to said first carrier lens and to said second carrier lens, wherein a person wearing said eyeglass frames can view an object through said first region, said second region or said optical telescope assembly.

* * * * *